US00RE34326E

United States Patent [19]

van Blerkom

[11] E Patent Number: Re. 34,326

[45] Reissued Date of Patent: Jul. 27, 1993

[54] ENCAPSULATION OF SPERM FOR ARTIFICIAL INSEMINATION

[75] Inventor: Jonathan van Blerkom, Denver, Colo.

[73] Assignee: British Technology Group, USA, Inc., Gulph Mill, Pa.

[21] Appl. No.: 612,387

[22] Filed: Nov. 14, 1990

Related U.S. Patent Documents

Reissue of:

[64] Patent No.: 4,840,891
Issued: Jun. 20, 1989
Appl. No.: 903,120
Filed: Sep. 3, 1986

[51] Int. Cl.[5] ..... A01N 1/02; A61K 35/52

[52] U.S. Cl. ..... 435/2; 435/177; 435/182; 424/561; 600/35

[58] Field of Search ..... 435/2, 174, 177, 180, 435/182, 240.2; 424/422, 424, 426, 430, 490, 561; 600/35

[56] References Cited

U.S. PATENT DOCUMENTS

| | | | |
|---|---|---|---|
| 3,608,549 | 1/1970 | Merrill | 424/426 |
| 3,712,303 | 1/1973 | Merkt et al. | 600/35 |
| 3,822,238 | 7/1974 | Blair et al. . | |
| 3,975,350 | 8/1976 | Hudgin et al. . | |
| 4,156,066 | 5/1979 | Gould . | |
| 4,156,067 | 5/1979 | Gould . | |
| 4,164,560 | 8/1979 | Folkman et al. | 435/182 |
| 4,255,550 | 3/1981 | Gould . | |
| 4,352,883 | 10/1982 | Lim | 435/240.22 |
| 4,391,909 | 4/1983 | Lim | 435/175 |
| 4,407,957 | 10/1983 | Lim | 435/178 |

OTHER PUBLICATIONS

R. L. Nebel et al. Microencapsulation of Bovine Spermatozoa, *Journal of Animal Science* vol. 60, No. 6 (1985).

Nebel, et al.; J. Anim. Sci., 50:1631 (Jun. 1985).

Thomas and Kaufman, Dolphin Conferences, Elephant Midwives and Other Astonishing Facts About Animals; 39 (Jeremy P. Tarcher, Inc.: 1990).

The Audubon Society Encyclopedia of North American Birds; 880 (1987).

IMV, The French Paillette Technique, 29–32.

IMV, Insemination Artificielle: La Paillette Francaise; 7–15.

*Primary Examiner*—Sam Rosen
*Attorney, Agent, or Firm*—Iver P. Cooper

[57] ABSTRACT

Sperm are encapsulated in a nontoxic polymer which is freely flowing at body temperature and a gel or solid at temperatures of storage and transfer. On delivery to the reproductive tract, the polymer microcapsule liquifies and the sperm are released.

24 Claims, No Drawings

ENCAPSULATION OF SPERM FOR ARTIFICIAL INSEMINATION

Matter enclosed in heavy brackets [ ] appears in the original patent but forms no part of this reissue specification; matter printed in italics indicates the additions made by reissue.

FIELD OF INVENTION

The present invention relates generally to the storage, transport, maintenance and insemination of viable sperm.

BACKGROUND OF INVENTION

For breeding of animals, maximum fertilization is dependent upon precise insemination of sufficient numbers of healthy, viable sperm at the appropriate times. The decrease in fertilization due to poor timing of insemination may be a result of either a loss of sperm viability or a reduction in numbers of viable sperm available during the fertile life of the ovum. It is desirable to improve conception rates in artificially bred animals through the prolongation of viable sperm retention and release in the female reproductive tract.

Studies have already been undertaken by several laboratories to evaluate the efficiency of microencapsulation of spermatozoa as a means of enhancing sperm retention in the female following artificial insemination. Microencapsulation is based on the fact that large losses of sperm occur from and within the female during insemination, especially after the deposition of previously cryopreserved spermatozoa. The major causes of sperm disappearance appear to be leucocytic phagocytosis (engulfment of sperm by white blood cells which invade the uterus at the time of heat), and retrograde removal (expulsion of sperm from the uterus back through the cervix).

It has been postulated that microencapsulation will protect sperm from white blood cells and retrograde removal, and with appropriate capsule construction, could provide a prolonged release of sufficient numbers of sperm at a preprogrammed time to allow fertilization in a single insemination. Also, because sperm need not be cryopreserved prior to insemination, normal loss occurring as a consequence of thawing from the frozen state would not be a factor. This would allow for greater numbers of viable sperm to be deposited.

"Microencapsulation", as used herein, is defined as a process whereby small living cells are completely surrounded and enclosed by relatively inert materials to form a microcapsule. Microcapsules range in diameter from approximately 0.2 microns to several millimeters.

Microcapsules have been provided with both impermeable and semipermeable membranes, depending on the composition of the enclosed material and the use intended. The mechanism(s) for release were associated with leaching, erosion, rupture, or other such actions, depending upon construction of the capsule wall.

Nebel, et al., J. Anim. Sci., 60: 1631 (June 1985) reported the microencapsulation of bovine spermatozoa. Their microcapsules differed from those of the present invention in that they were not designed to assume a liquid state at a particular temperature. Sperm cells were suspended in a sodium alignate and fine droplets of this suspension were produced using a syringe pump extrusion technique. The droplets were collected in a calcium chloride solution which results in an immediate gellation of the droplets, thus producing a shape-retaining high viscosity mold for the microcapsules. A semipermeable membrane was applied to the droplets by suspending them in a solution of polylysine, thus forming the microcapsules. The gelled suspension of sperm inside the capsules was then liquified by exposing the capsules to a solution of sodium citrate, rather than by raising the temperature to body temperature. Once a sperm suspension in the capsule was liquified, the sperm resumed the mobility which had been arrested temporarily by gellation.

However, the sperm showed diminished motile life following such encapsulation and total loss of fertilizability. Further studies indicated that when biodegradable microcapsules were used, the retention of the sperm was poor. The biodegradable microcapsules were also prone to early rupture and retrograde removal.

Drug delivery means which are solid or gel-like at room temperature and liquid at body temperature are known. These do not allow for providing nutrients and oxygen to living cells to maintain their viability. Also, they do not provide or require a sharp phase transition with respect to temperature.

The present invention contemplates the encapsulation of living, viable sperm such that the sperm's motility, viability, retention and release in the female reproductive tract is not significantly impaired.

SUMMARY OF THE INVENTION

The invention contemplates the storage, transportation, and maintenance of sperm cells in a viable state for relatively prolonged periods of time, and their delivery in viable form to the female reproductive tract. Purified sperm are encapsulated in a nontoxic, hydrophilic polymer, the polymer being permeable to gases and small molecules (5000 daltons or less) and relatively impermeable to macromolecules. The polymer must assume a flowable liquid state at the body temperature of the recipient (typically 37° C.) and exist in a solid or semisolid gel state at temperatures below such body temperature.

The polymer, is preferably a reversible hydrogel of a water insoluble, hydrophilic, polyurethane polymer.

An ideal encapsulating polymer would have the following characteristics:

[1] nontoxicity, the polymer must have a chemical composition that will be inert to cells and be unable to elicit an immune response when placed in situ;

[2] programmability, the polymer must be able to change its physical state as a function of an environmental factor such as temperature, pH, specific ion concentration. The desired change in physical state is from a waterlike fluid to-viscous fluid-to a solid gel (and vice versa) over a predetermined period of time, and under a predetermined environmental condition, such as temperature;

[3] matrix formation, the polymer must be composed nearly entirely of water, have a predetermined porosity, freely exchange gas and molecules of low molecular weight (metabolites) and be able to maintain a constant pH throughout the matrix;

[4] cryopreservability, the polymer when fully formed with cells enclosed should be able to be prepared for routine cryopreservation in liquid nitrogen without irreversible alteration in structure or physical properties and without significant damage to cellular contents; and

[5] deliverability, the polymer must be able to get prepared in such a form as to make its delivery or deposition within the reproductive tract relatively fast and simple.

The microcapsule must be permeable to small molecules so that nutrients, including oxygen, may reach the sperm, and so waste products, including carbon dioxide, may be eliminated. Preferably, the polymer provides a molecular weight cutoff of about 5,000 daltons.

While the encapsulated sperm may be maintained for a time at room temperature, in order to reduce the rate of build-up of potentially toxic metabolites within the microcapsule, the encapsulated sperm are preferably kept at lower temperatures, such as 4° C.

In general, a more solid gel is preferable, since it will more narrowly constrain the movement of the sperm within the microcapsule. By arresting the movement of the sperm, its metabilic activity is reduced, with the aforestated advantages.

The microcapsule must be as free as possible of substances toxic to either the sperm or the recipient animal. In this regard, it is important that the polymer be washed thoroughly to remove toxic chemicals, such as the diisocyanate used in the preparation of a polyurethane polymer.

Success in fertilization is very dependent upon the pH in the uterus. It is undersirable to deliver sperm to the uterus in a manner which adversely affects pH. The culture medium in which the sperm reside when encapsulated should have a pH in the desired range 7.2 to 7.6.

It is desirable that the microcapsule be translucent so that the condition of the sperm is observable by phase contrast or differential interference contrast microscopy.

As used herein, the term "animal" is intended to include humans. *A "warm-blooded animal" is one whose reproductive tract temperature is normally substantially in excess of room temperature (22° C.).*

While the body temperature of animals typically selected for artificial insemination is generally 37° C., it is possible that particular species or individuals will evince body temperatures markedly below or above this figure. In this event, it is within the contemplation of this invention to modify the composition of the encapsulating polymer so that its state transition occurs at a higher or lower temperature.

DETAILED DESCRIPTION OF THE INVENTION

In the present invention, sperm are encapsulated in porous or semipermeable hydrophilic polymer that is relatively inert to the cells it surrounds and to the site into which it is deposited, such that an immune response does not take place, In addition, the hydrophilic polymer is designed to maintain a constant pH throughout its matrix, to allow free passage of low molecular weight molecules such as carbon dioxide, oxygen, glucose and amino acids through its pores and to form a protective barrier against cells or macromolecules, or both, which could engulf, attack, or react with the encapsulated sperm. The polymer preferably provides a sufficient protective environment around the sperm so that they are able to survive at temperatures as low as 4° C.

Release from the encapsulate is fast and simple. Merely by putting the capsule into an environment maintained at approximately 37° C., the polymer progressively becomes liquid, thereby freeing the sperm to swin away.

For the purposes of this invention a variety of thermally reversible hydrophilic polymers are satisfactory. In the preferred embodiment of the invention, the polymer is a thermally reversible hydrogel, being a flowable liquid (sol) at the body temperature of the recipient, typically about 37° C. but a solid semigel at the lower temperatures experienced during storage and transportation, typically about 15° or less. The polymer must be water insoluble at normal ambient temperatures but still absorb water. The preferred polymers are the polyurethane-polyether polymers that are readily prepared by the reaction of long chain polyoxyethylene diols or glycols with polyfunctional isocyanates. The polymers may be modified by the addition of uarrcus functional groups, such as lactone groups, carboxylate groups and/or hydroxyl groups in the polymer backbone. Such modifications can be used to tailor the characteristics of the polymer, for example, its permeability and translucency. In general, the polymers are prepared by preparing a homogeneous melt or mixture of the long chain polyoxyethylene diol (polyether and/or polyester) and a low molecular weight glycol and reacting the melt or mixture with a diisocyanate.

The preparation of the water insoluble, hydrogel forming, hydrophilic polyurethane and modified hydrophilic polyurethane polymers is disclosed in numerous patents such as, for example, U.S. Pat. Nos. 3,822,238; 3,975,350; 4,156,066; 4,156,067 and 4,255,550; the disclosures of which are incorporated herein by reference. Since the preparation of these polymers form no part of the present invention, only the preparation of representative polymers of this class which are satisfactory for the purposes of the present invention are described below.

A convenient source of the polyether moiety of the preferred polymers are the various grades of Carbowax (R) polyoxyethylene glycols (Union Carbide Corporation, Danbury, CT) and the Pluronic (R) block copolymers of ethylene oxide and propylene glycols (Wyndotte Corporation, Parsippany, NJ). A convenient source of a satisfactory diisocyanate is methylene bis-cyclo-hexyl-4,4'-diisocyanate (Desmodur W of Mobay Chemical Corporation, Pittsburgh, Pa.). Catalysts useful in forming the polymer include dibutyl tin dilaurate and stannous octoate (T12 and T9, respectively, of Metal and Thermite Company, Rahway, N.J.).

To prepare the encapsulated sperm, the sperm are suspended in the desired aqueous culture medium, and are encapsulated in the polymer hydrogel by slowly mixing the suspension with the hydrogel in flowable liquid state at normal animal temperatures and the mixture chilled, typically over a period of 0.5 to 18.5 hours, to a temperature sufficiently low to allow the hydrogel to revert to or set into its solid gel state. For example, the mixture may be formed at a temperature of around 37°-39° C. and the mixture gradually chilled over a period of minutes to hours, depending on the source (species) of sperm, to normal room temperature, 22° C., but preferably to a lower temperature such as 4°-5° C. The encapsulated sperm are completely immobilized in the polymer and may be stored and transported at the lower temperatures to the site of use. The microcapsule preferably provides a gaseous atmosphere of 5% $O_2$, 5% $CO_2$, and 90% $N_2$ and a pH of 7.25-7.35. This may be accomplished by equilibrating the polymer with the desired atmosphere and storing it in a sealed container in a medium buffered to proper pH. In preparing the polymer hydrogel, the water or aqueous phase preferably is comprised of culture medium, preferably buffered to maintain a pH of 7.37–7.42, and containing nutrients to sustain minimal metabolic needs of the sperm. A typical aqueous culture medium is Ham's F10 solution with half the normal glucose concentration, but the invention herein is not limited to any particular culture medium. Preferably, calcium lactate is added to the culture medium shortly before the sperm are encapsulated by polymerization.

Upon introduction of the capsule of sperm by standard artificial insemination methods, the temperature rises to the uterine body temperature of the recipent, whereby the hydrogel progressively reverts to its flowably liquid state and releases the sperm over a predetermined length of time.

EXAMPLE 1

Determining the Suitablity of a Polymer for Gamete Storage

In considering the suitability of various polymers for gamet storage, several physical conditions were thought desirable: (1) the polymer must allow free passage of metabolites, small molecules, and gasses to maintain uniform chemical composition and pH; (2) the polymer must undergo phase transition at a predictable rate and time; and (3) the polymer must have a fairly uniform porosity preferably not greater than 1 micron.

PERMEABILITY

Permeability was determined by incubating polymer cubes from 1 to 9% concentration in medium containing $S^{35}$-L-methionine. At 5 minute intervals polymer was removed and a 0.5 mm core sample was obtained. Radioactivity in the core was determined by liquid scintillation spectroscopy. The results of a typical run with three concentrations of polymer are presented in Table 1.

TABLE 1

| ACCUMULATION OF 35S METHIONINE IN CENTER OF POLYMER | | | |
|---|---|---|---|
| | POLYMER CONCENTRATION | | |
| | 1% | 5% | 9% |
| TIME (MINUTES) | TOTAL RADIOACTIVITY (CPM × 1 MILLION) | | |
| 1 | 2.8 | 3.5 | 3.2 |
| 5 | 12.7 | 16.8 | 14.7 |
| 10 | 13.9 | 17.4 | 15.2 |
| 15 | 12.4 | 16.8 | 13.3 |
| 30 | 17.2 | 15.1 | 14.7 |
| 45 | 16.5 | 15.8 | 15.3 |

These results demonstrate that concentration of polymer has no visible influence on rate of accumulation of radioactivity in center of a 5 mm cube and that substantial equilibrium with the environment requires less than 5 minutes

Maintenance of pH

Maintaining a constant and uniform pH throughout the polymer is absolutely required for survival of mammalian gametes. To test the ability of polymer to assume pH, polymer was gelled around a micro pH electrode at a adminal pH of 7. The polymer-electrode assembly was then placed in culture medium made at pH ranging from 5.5 to 8.5 (ambient pH). The rate of change of pH from a nominal pH 7 to ambient pH was measured. In polymer concentrations of 1,4 and 9%, pH change to ambient at the core occurred within 45 seconds. This result demonstrates that the entire polymer can respond rapidly to changes in environmental pH.

Porosity

Preferably, the polymer used for entrapment of spermatozoa had an average pore size of no more than one micron, although porosities up to 4 microns in diameter should be acceptable. To determine approximate, relative porosity as a function of polymer concentration, blocks of polymer were quick frozen in liquid nitrogen and sectioned in an ulramicrotome maintained at liquid nitrogen temperature. The frozen thin sections were mounted on an electron microscope grid. Under standard conditions used to prevent artifactial shrinkage of specimens, the grids were critical point dried, whereby frozen water is replaced by liquid $CO_2$. The specimens were examined with a million volt electron microscope and approximate pore size distributions measured. The results are shown in Table 2.

TABLE 2

| POLYMER CONCENTRATION | APPROX. PORE SIZE RANGE |
|---|---|
| 1% | 5–8 microns |
| 2% | 5–8 microns |
| 3% | 2–4 microns |
| 4% | 1–3 microns |
| 4.5% | 1–2 microns |
| 5.5% | 0.5–1.5 microns |
| 6% | 0.3–1.5 microns |
| 8% | less than 0.5 microns |

Phase Transition

Polymer at concentrations of 4% and 8 % (W/V) were utilized for studies polymers of the rate of transition to complete gelation [S] or liquification [L]. The results for these studies are shown in Table 3.

TABLE 3

| TIMING OF PHASE TRANSITION | | |
|---|---|---|
| | 4% | 8% |
| SOLID TO LIQUID TIME (4-37C) (Minutes) | | |
| 5 | S | S |
| 10 | S | S |
| 15 | S | S |
| 30 | S | S |
| 45 | S/L | S |
| 75 | L | S/L |
| 120 | L | L |
| LIQUID TO SOLID (37-4C) | | |
| 5 | L | S |
| 10 | S/L | S |
| 15 | S | S |

These results demonstrate that the transition from solid to liquid occurs much more slowly than the transition from liquid to solid.

EXAMPLE 2

Encapsulation of Spermatozoa

Polymers used in our studies include RL39-41; RL39-110; RL39-111; RL39-114; RL39-115; RL39-117; and RL39-118 (Tyndale Plains-Hunter Ltd.) Polymer concentrations ranged from 1.5 to 11.5%. For these trials, polymers RL39-115, 117 and 118 demonstrated a rate of cooling to final hardness sufficient to maintain at least 60% of the encapsulated spermatozoa in a viable state.

Sperm used in this study were from mouse, bull and human sources.

It was demonstrated that spermatozoa could be maintained in the polymer microcapsule for as many as 10 days at 10° C., and upon return to a liquid phase during a 12 hour incubation at 37° C., motility resumed in 80 percent of the cells. Subsequently, it was demonstrated by in vitro fertilization that some of these sperm retained the ability to fertilize an oocyte. Similar motility observations were made with human spermatozoa but in vitro fertilization was not attempted.

The following protocol was employed with mouse sperm; 10.7 gms of polymer RL-39-115 was added to 50 ml of culture grade water. The polymer was fully hydrated and sterilized by high temperature and pressure. Concentrated medium was added, the polymer stirred vigorously and gradually cooled to 38° C. The final polymer concentration was 5.35%. At 38° C., 200 million sperm contained in 80 μl were added to the polymer solution and stirred vigorously for 5 minutes. The polymer-sperm dispersion was poured into molds of various shapes (3×35 mm cylinders; 5×15×40 rectangles), and the molds placed in a gas tight incubator at 37° C. containing 90% $N_2$; 5% $CO_2$; 5% $O_2$. This incubated chamber was cooled at a controlled rate ranging from 0.5° C./min. to 15° C./min. Final temperatures attained ranged from 15° C. to 3° C. Observations of sperm activity were made by means of a time-lapse video system attached to a Nikon Diaphot microscope equipped with differential interference contrast optics (NORMARSKI) and a Dage television camera. Observations were made at 5 minute intervals during cooling and continuously during reheating. The microscope stage was enclosed by a small chamber that precisely maintained temperature and held a specific gaseous atmosphere (90% $N_2$ 5% $O_2$ 5% $CO_2$) during all operations. Reheating occurred over a period ranging from 5 minutes to 18 hours.

Depending upon the rates of heating and the species, movements of spermatozoa generally preceded total liquification of polymer. Mouse sperm (as well as human and bovine) prepared in this manner had no apparent kinetic activity when microcapsule temperature in polymer reached 7° C., at which time the polymer was fully gelled. Upon reheating, activity was first observed at 20° C. at which time the polymer was in a semi-gel state. Sperm activity did not return uniformly throughout the capsule but rather first appeared at the peripheral regions of the capsule and lastly at the more interior regions. Kinetic activity was a function of liquification, the process being more complete at the periphery and proceeding to the interior with time. Sperm obtained from the reheated capsule were mixed with fresh medium, centrifuged at 500 g for 10 min., and then allowed to "swim" away from the centrifugate obtained from centrifugation. Some of the mouse and bovine sperm so obtained were shown to be capable of fertilizing a suitably mature oocyte in vitro.

Human sperm was prepared in same way and tested in same fashion. Viability was assessed by morphology, general motility and the appearance of active foward progressive motility. No fertilizations were attempted with human spermatozoa.

EXAMPLE 3

Encapsulation of Bovine Spermatozoa

Polymer at a concentration of 3.8% (dry weight/liquid) in culture medium containing salts, lactate, pyruvate but not glucose or fructose was used. Bovine in spermatozoa encapsulated in the polymer were preferably cooled from 37° C. to 10° C. over a period of at least 6 hours, a much slower rate than that found to be effective for encapsulated murine or human spermatozoa. The preferred rate of temperature increase for restoring the motility of bovine spermatozoa (gel to liquid transformation) is also longer than for encapsulation of spermatozoa of the other two species (12–16 hours, in the polymer capsules formed with RL39-117, RL39-118, and RL39-115). At present, bovine spermatozoa have been maintained over an 18 hour period. At least 70% of the spermatozoa displayed the typical pattern of activated, progressive, forward motility characteristic of viable sperm after being released from the polymer at 37° C. Successful in vitro fertilization of in vitro matured bovine oocytes demonstrated that these sperm are in fact, capable of fertilization of an occyte.

EXAMPLE 4

Sperm Mortality as Function of Retention Time

Bovine sperm obtained from a "swimup column" were diluted with polymer to a final density of approximately 6000/ml in a rectangular mold 10 mm×25 .nm×5 mm. The liquid polymer was gelled in an autmosphere of 90% $N_2$, 5% $CO_2$ and 5% $O_2$ with the temperature brought to 7° C. over a period of 5 hours. The molds were kept at refrigerator temperatures for as many as 14 days, after which time, they were placed on the stage of an incubator enclosed microscope at 10° C. The temperature was increased gradually to 37° C. over a period of 3 hours. Throughout this period continuous time-lapse video recording was accomplished. The first signs of sperm motility were observed at 8 hours when tail movement became apparent. By 10 hours vigorous tail motion was observed and while the polymer was still in semigel state, sperm head motion was apparent. By 12 hours approximately 40% of the sperm showed complete motility with at least half presenting progressive forward activated motility. By 14 hours the polymer was completely liquified and sperm motion essentially normal. Loss of spermatozoa (nonmotile; abnormal gross morphology) was approximately 25–30%. In some experiments, sperm loss ranged from a low of 20% to a high of 71%. The typical incidence of sperm loss as a function of time in polymer is shown in Table 4.

TABLE 4

SPERM MORTALITY AS A FUNCTION OF TIME IN POLYMER

| TIME (DAYS) | % VIABLE |
|---|---|
| 1 | 85 |
| 2 | 85 |
| 3 | 85 |
| 5 | 85 |
| 8 | 71 |
| 10 | 50 |
| 14 | 48 |

EXAMPLE 5

Effect of Polymer Concentration

Another important series of experiments demonstrates the critical association between polymer concentration and retention of viability. With small incremental increases in polymer concentration, viability, as judged from sperm morphology and motility patterns after release from polymer, decreases dramatically. The results of a typical experiment in this series, utilizing polymer RL39-110, are presented in Table 5.

TABLE 5

| CORRELATION BETWEEN POLYMER CONCENTRATION AND SPERM VIABILITY | |
|---|---|
| CONCENTRATION (%) | % VIABLE* |
| 1 | 75 |
| 1.5 | 75 |
| 3.5 | 68 |
| 4.0 | 50 |
| 5.0 | 42 |
| 6.5 | 20 |
| 8.5 | 0 |

*after 4 days in polymer at 7C with 18 hr warm period

These results demonstrate the critical nature of polymer concentration and formulation for successful preservation of spermatozoa. For example, similar studies showed that polymers RL39-110 and 111 were well suited for preservation of mouse and human sperm, but not for bovine. This points out the importance of testing various polymer formations as taught above in optimizing the capsule for a new species.

EXAMPLE 6

Effect of Heating and Cooling Rates

In another series of polymer experiments, the correlation between rates of cooling and heating on sperm viability was determined. All assays were performed with sperm entrapped in polymer for 5 days at 7° C. The influence of cooling rate is shown in Table 6 and heating in Table 7.

TABLE 6

| SPERM VIABILITY AS A FUNCTION OF COOLING RATE | |
|---|---|
| TIME (HRS) REQUIRED TO COOL TO 7C | % VIABILITY |
| 3 | 24 |
| 5 | 32 |
| 8 | 59 |
| 12 | 60 |
| 16 | 74 |

TABLE 7

| SPERM VIABILITY AS A FUNCTION OF RATE OF HEATING | |
|---|---|
| TIME (HRS) TO 37 C | % VIABILITY |
| 3 | 0 |
| 6 | 27 |
| 10 | 42 |
| 14 | 55 |
| 16 | 79 |
| 18 | 80 |

These experiments utilized formulation RL39-114 at 4.5% concentration.

EXAMPLE 7

Preparation of a typical polyurethane-polyether polymer (RL39-118)

The polyether moiety was prepared by mixing 136 grams of polyoxyethylene glycol (Carbowax 8,000) and 3.8 grams of diethylene glycol with stirring at 77° C. to form a homogeneous melt. The temperature was allowed to decrease to 65° C. While continuing the stirring, 16.63 grams of methylene biscyclohexyl-4,4'diisocyanate were added. When the temperature decreased to 60° C., 0.15 cc of dibutyl tin dilaurate (T12) was added and the mixture allowed to heat up to about 70° C. The reaction mass was then poured into a polypropylene pan. Upon completion of the pouring operation, the pan was placed in an air circulating oven at 100° C. and maintained in the oven for one hour to cure the polymer.

After cooling the mass to ambient room temperature, the polymer mass was cut into small pieces. A sufficient amount of the small pieces was mixed with water to form a mixture containing 2% to 5% solids. The mixture was stirred while increasing the temperature of the mixture to 95° C. wherein the polymer comes out of solution and agglomerates. The temperature is then reduced with continuous mixing to produce a shearing action; preferably by hand.

As the solution cools to about 70°-75° C. it begins to become clearer as the polymer begins to redissolve. As the temperature continues to fall, the solution increases in viscosity and becomes almost transparent. The cooling is stopped near 30° C. and the solution gel. If this has not produced a gel that is homogeneous, the cycle may be repeated.

The softening point and rigidity of each type of gel can be altered by changing the precent of solids of the resin. Higher resin content produced more rigid and higher softening point gels.

The gel is then made into a dry form which is reconstituted with culture medium. First the gel is spread out on a suitable nonstick substrate such as polypropylene or polyethylene to a thickness of about 1/16". The gel is then dried to produce a thin pliable film. This film is easily cut or torn into small pieces, or can be prepared in a powder form. The drying can take place in a vacuum oven at room temperature, a circulating oven at or below 50° C., or in a freeze dryer. The resulting dry polymer film is then cut into small pieces and warm water at about 35°-45° C. is added and stirred for about five minutes or until all the polymer is in solution to produce the desired solids content.

The gel will reach its final rigidity at room temperature in about one hour. Air bubbles can be rapidly removed from the gel by centrifugation or storing in a closed container at 40° C. for 6-12 hours. After several washes with deionized $H_2O$ to remove any toxic substances that may have been produced during the preparation of the polymer, the dried polymer can be reconstituted with any culture media that will support spermatozoa in vitro.

A hydrogel containing 5% of the above described polymer with an aqueous culture medium is a flowable, somewhat syrupy liquid at 37° C. but when cooled to room temperature (20°-22° C.) sets into a solid gel. The liquid hydrogel may be brought to the desired pH for a specific sperm by the addition of a buffer solution or a dilute acid or alkaline solution as may be appropriate.

RL39-117 is prepared identically except for the use of 76.5 g of Carbowax 4500.

I claim:

1. A method of encapsulating viable [mammalian] *vertebrate animal* sperm for storage or transfer, and subsequent insemination of a female [mammal] *vertebrate animal*, which comprises encapsulating the sperm with a nontoxic hydrophilic polymer, said polymer being essentially freely flowable at the *normal* temperature of the [uterus] *reproductive tract* of such [mammal] *vertebrate animal, which temperature is substantially greater than 22° C.*, but not freely flowable at the temperature of storage or transfer, *the latter tempera-*

*ture not being substantially greater than 22°C.*, the polymer at the latter temperature being permeable to molecules of a predetermined size but not to the sperm whereby the sperm may receive nutrients and excrete waste products through the microcapsule without escaping; the sperm escaping from the microcapsule at said [uterine] *reproductive tract* temperature when the polymer becomes freely flowable.

2. The method of claim 1, wherein the transition of the polymer to the liquid state is completed within 14 hours after it is brought to 37° C.

3. The method of claim 1, wherein the sperm are encapsulated by (a) providing viable sperm suspended in a suitable culture medium, (b) adding the polymer to the said sperm suspension, transferring the mixture into molds corresponding to the desired dimensions of the microcapsules, and (c) cooling the mixture until it solidifies into a non-free flowing gel.

4. A method of inseminating [an] *a vertebrate* animal *whose normal reproductive tract temperature is substantially greater than 22°*, which comprises inseminating a receptive female of a species of *said* animal with the encapsulated sperm of claim 1, [said female] *and* permitting the encapsulated sperm to warm to the temperature of the [uterus] *reproductive tract* of the female, at which temperature the capsule is [liquiified] *liquified* and the sperm released.

5. The method of claim 4 in which the sperm are first held at a temperature at which the capsule is essentially solid.

6. An article of manufacture comprising viable sperm of a [mammalian] *vertebrate animal* species *whose normal reproductive tract temperature is substantially greater than 22° C.*, encapsulated in a microcapsule formed by a nontoxic hydrophilic polymer which is essentially solid at 4° C., said sperm being released by liquefaction of said polymer at the temperature of the [uterus] *reproductive tract* of females of such species, said sperm remaining capable of fertilizing such females after such encapsulation and release.

7. The article of claim [4] 6, wherein the polymer is a polyurethane polymer.

8. The [method] *article* of claim 7, wherein the polymer is selected from the group consisting of polyurethane polyoxyethylene and polyurethane polyester polymers.

9. The article of claim [4] 6 in which said microcapsule encloses an atmosphere which is about 5% $O_2$, 5% $CO_2$ and 90% $N_2$.

10. The article of claim [4] 6 in which the polymer is selected from the group consisting of RL39-115, RL39-117, and RL39-118.

11. The article of claim [4] 6 in which the polymer forms a microcapsule enclosing a culture medium for the sperm, said medium having a pH of about 7.37–7.42.

12. The article of claim [4] 6 in which the polymer forms a microcapsule enclosing a culture medium for the sperm, said medium provding calcium lactate in an amount sufficient to render the sperm hypermotile when unrestrained by the microcapsule.

13. The article of claim [4] 6 where the polymer forms a translucent microcapsule about the sperm, whereby its motility may be observed.

14. The article of claim 6 wherein the sperm are held in a state of reduced motility and metabolic activity prior to liquefaction, the motility and metabolic activity of the sperm being restored after liquefaction.

15. The article of claim 6, where more than 50% of the sperm remain viable for 14 days after encapsulation and storage at 4° C.

*16. The method of claim 1 in which the animal is a mammal.*

*17. The method of claim 4 in which the animal is a mammal.*

*18. The article of claim 6 in which the animal is a mammal.*

*19. The method of claim 1 in which the animal has a normal reproductive tract temperature of at least about 37° C.*

*20. The method of claim 4 in which the animal has a normal reproductive tract temperature of at least about 37° C.*

*21. The article of claim 6 in which the animal has a normal reproductive tract temperature of at least about 37° C.*

*22. The method of claim 19 in whic the animal has a normal reproductive tract temperature of about 37° C.*

*23. The method of claim 20 in which the animal has a normal reproductive tract temperature of about 37° C.*

*24. The article of claim 21 in which the animal has a normal reproductive tract temperature of about 37° C.*

* * * * *